United States Patent
Sasges et al.

(10) Patent No.: US 11,807,833 B2
(45) Date of Patent: Nov. 7, 2023

(54) PH DEPENDENT SOLUBLE POLYMERS

(71) Applicant: Trojan Technologies Group ULC, London (CA)

(72) Inventors: Michael R. Sasges, Victoria (CA); Anthony Martin John Porter, London (CA)

(73) Assignee: TROJAN TECHNOLOGIES GROUP ULC, London (CA)

( * ) Notice: Subject to any disclaimer, the term of this patent is extended or adjusted under 35 U.S.C. 154(b) by 121 days.

(21) Appl. No.: 17/177,758

(22) Filed: Feb. 17, 2021

(65) Prior Publication Data

US 2022/0259526 A1 Aug. 18, 2022

(51) Int. Cl.
| | | |
|---|---|---|
| *B08B 9/023* | (2006.01) | |
| *C11D 17/04* | (2006.01) | |
| *C11D 7/08* | (2006.01) | |
| *C11D 11/00* | (2006.01) | |
| *A61L 2/26* | (2006.01) | |
| *A61L 2/10* | (2006.01) | |
| *C02F 1/32* | (2023.01) | |
| *B08B 1/00* | (2006.01) | |

(Continued)

(52) U.S. Cl.
CPC .............. *C11D 17/043* (2013.01); *A61L 2/10* (2013.01); *A61L 2/26* (2013.01); *B08B 1/006* (2013.01); *B08B 3/08* (2013.01); *B08B 9/023* (2013.01); *C02F 1/325* (2013.01); *C11D 7/08* (2013.01); *C11D 7/266* (2013.01); *C11D 11/0041* (2013.01); *C11D 17/049* (2013.01); *A61L 2202/11* (2013.01); *B08B 2209/02* (2013.01); *C02F 2201/324* (2013.01); *C02F 2303/04* (2013.01)

(58) Field of Classification Search
CPC ......... C11D 17/043; C11D 7/08; C11D 7/266; C11D 11/0041; C11D 17/049; A61L 2202/11; A61L 12/10; A61L 2/26; B08B 1/006; B08B 3/08; B08B 9/023; B08B 2209/02; C02F 2201/324; C02F 2303/04; C02F 1/325
See application file for complete search history.

(56) References Cited

U.S. PATENT DOCUMENTS 6,342,188 B1   1/2002 Pearcey et al.
6,659,431 B1 * 12/2003 Fang ..................... B08B 9/023
                                                   422/906

(Continued)

FOREIGN PATENT DOCUMENTS

CA         2432240 A1      1/2004
WO    WO-2012140438 A1 * 10/2012 ............. A01N 25/26

*Primary Examiner* — Sharidan Carrillo
(74) *Attorney, Agent, or Firm* — Ference & Associates LLC (57) ABSTRACT

An embodiment provides a method for cleaning a surface, including: encapsulating a cleaning composition in a polymer material to form a compound, wherein the polymer material surrounds the cleaning composition; placing the compound in a location adjacent to the surface, wherein the location adjacent to the surface is a volume separated from an outer volume; dissolving the polymer material at a pH above a target value above the polymer material pH dissolution point, wherein the dissolving releases the cleaning composition; and cleaning the surface using the released cleaning composition. Other aspects are described and claimed.

8 Claims, 4 Drawing Sheets

11. Quartz sleeve
12. Seals
13. Inner volume
14. Outer volume
15. Canister
16. Cleaning compound
17. Wiper (51) Int. Cl.
*B08B 3/08* (2006.01)
*C11D 7/26* (2006.01)

(56) References Cited

U.S. PATENT DOCUMENTS

| | | | |
|---|---|---|---|
| 6,863,078 B1 * | 3/2005 | Dall'Armi | B08B 9/023 |
| | | | 134/122 R |
| 9,029,798 B2 | 5/2015 | O'Keefe | |
| 9,567,243 B2 | 2/2017 | Elku et al. | |
| 2001/0031714 A1 | 10/2001 | Gassenmeier et al. | |
| 2005/0226826 A1 | 10/2005 | Eason et al. | |
| 2012/0097187 A1 | 4/2012 | Penhale et al. | |
| 2013/0217609 A1 * | 8/2013 | Fernandes | C11D 17/0039 |
| | | | 510/438 |
| 2017/0298216 A1 * | 10/2017 | Labeque | B65D 81/3261 |
| 2022/0259526 A1 * | 8/2022 | Sasges | C11D 17/049 |

* cited by examiner

11. Quartz sleeve
12. Seals
13. Inner volume
14. Outer volume
15. Canister
16. Cleaning compound
17. Wiper

FIG. 4

PH DEPENDENT SOLUBLE POLYMERS

BACKGROUND

This application relates generally to pH sensitive soluble polymers, and, more particularly, to pH dependent soluble polymers for releasing an acid composition to clean a component of a water treatment system.

The proper disinfection of water is critical to ensure water quality. As the need for cleaner sources of water has increased, water disinfection methods have evolved to match the rising challenge. Water supplies may contain heavy metals, sediment, chemicals, pesticides, or the like. Water sources may also contain pathogens such as microorganisms, viruses, or the like. Left untreated, such water may be unhealthy or unsafe for use by humans or animals. Ultraviolet (UV) light treatment of water may be used to treat contaminants or to inactivate pathogens. Water may pass through an open channel or through a closed vessel where the water is subjected to UV light. The UV treatment may damage nucleic acids of the pathogens. The disruption of the genetic material may render the pathogens incapable of performing vital cellular functions, thereby rendering them harmless. Thus, this UV process may make water potable despite the water source containing microorganisms, viruses, or the like. UV treatment systems often require a UV-transparent material such as fused silica or fluoropolymer that separates the UV source from the water to be treated. Materials from the water, including minerals or organic materials may foul the wetted surface of the UV-transparent material, thereby degrading the performance of the system. In order to restore or maintain performance, the UV light treatment systems and associated components may require cleaning due to fouling.

BRIEF SUMMARY

In summary, one embodiment provides a method for cleaning a surface, comprising: encapsulating a cleaning composition in a polymer material to form a compound, wherein the polymer material surrounds the cleaning composition; placing the compound in a location adjacent to the surface, wherein the location adjacent to the surface is a volume separated from an outer volume; dissolving the polymer material at a pH above a target value above the polymer material pH dissolution point, wherein the dissolving releases the cleaning composition; and cleaning the surface using the released cleaning composition.

Another embodiment provides a device for cleaning a surface, comprising: a cleaning composition comprising a polymer material encapsulating an acid composition, wherein the polymer material dissolves at a pH above a target value above the polymer material dissolution point releasing the acid composition to clean a location adjacent to the surface where the cleaning composition is placed, wherein the location comprises a volume separated from an outer volume.

A further embodiment provides a device for cleaning a surface, comprising: a canister comprising a compartment housing a cleaning composition, wherein the compartment separates the cleaning composition from a remaining portion of the canister and wherein the compartment is adjacent to a component to be cleaned; the cleaning composition comprising a polymer material encapsulating an acid composition, wherein the polymer material dissolves at a pH above a target value above the polymer material dissolution point, thereby releasing the acid composition to clean the component.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

UV water treatment systems are a cost effective and efficient method to treat water. One treatment includes UV disinfection. UV disinfection may protect against water borne viruses, bacteria, molds, or the like. Additionally, UV disinfection may be effective against disease causing organisms such as giardia and cryptosporidium. Proper control of UV light delivered to a volume of water may be essential to the proper treatment of the water. In other words, effective exposure of contaminated water to a UV source may be critical to proper disinfection of a water source. While the majority of this discussion is directed toward UV disinfection, it should be understood that the method and system as described herein extends to any UV treatment, not just disinfection.

UV wavelength may be in the range of 100 to 400 nanometers, which can be provided by a variety of UV light sources, for example, UV light emitting diodes (LEDs), arc lamps, mercury vapor lamps, or the like. Conventional UV light source arrangements vary depending on the application. For example, a residential UV light source may be used to treat well water or other non-municipal water source. Residential units may have a chamber containing a UV light source piped in-line between a water source, such as a well, and the household piping. A residential system may have one or more UV lights that expose the water to UV light as the water passes through the UV purification chamber. Residential systems may be designed for the relatively lower volume of water used by a home as compared to a larger industrial or commercial UV treatment system. Larger UV treatment systems may be found in industrial or commercial facilities such as a municipal water treatment facility. The larger systems may handle large volumes of water, and may, therefore, have a plurality of UV lamps, for example, as arranged in an array. These UV light sources may be arranged in or around vessels of water to be treated with UV light. Commercial systems may have multiple vessels or tubes through which water passes for UV treatment.

For ease of readability, this disclosure focuses mainly, but not solely, on the application of UV treatment of water for the disinfection of drinking water. However, other implementations of the systems and methods described herein are possible and contemplated. For example, since UV light may be used to disinfect surfaces, the described systems and methods may be used in such an application. These surfaces may include areas used to prepare sensitive materials in which organisms or organic residue would contaminate the surface such as a biological hood, surgical suite, food preparation area, clean room, or the like. Additionally, the described system and method may be used for the disinfection of pool water, the disinfection of a gas (e.g., UV light may be used to purify air), contaminated soil, in advanced oxidation or environmental contaminant treatment (ECT) applications, ionization of organic molecules, and the like. Thus, the examples described herein regarding the disinfection of water are merely illustrative. Other uses are contemplated and disclosed.

Conventional UV disinfection systems do have some drawbacks. UV disinfection may rely on the ability of a proper amount of UV light to reach the volume of water to be treated. For example, a UV lamp must have the proper output of UV light to be effective. If a UV lamp, lens, sleeve, or the like begins to foul, the water may not be properly treated, because the UV lamp is no longer transmitting a necessary amount of UV light. In other words, a UV lamp may foul over time and, thereby, reduce the UV light output provided by the UV lamp. To reduce fouling of quartz sleeves, surface, or UV-transparent material, many approaches have been used. For example, an acid gel may be loaded in a canister. The gel may slow dissolution into an outer volume outside the canister. The gel may leak from the canister. What is needed is a system and method to control the release of acid to clean the sleeve when necessary based upon a pH within the canister.

Acidic compounds such as phosphoric acid may be used to remove fouling materials from components in the UV light treatment systems, see U.S. Pat. Nos. 6,518,577, 6,863, 078, 6,872,954, and 9,567,243 the entire contents of which are incorporated by reference here. These acids may be retained within canisters that are moved or wiped across the surfaces to be cleaned, see U.S. Pat. No. 10,322,947 the entire contents of which are incorporated by reference here. Such canisters invariably have leakage, resulting in loss of acid-based cleaners. One approach to mitigate this loss is to incorporate the acid into a shear-thinning gel, see U.S. Pat. No. 7,018,975 the entire contents of which are incorporated by reference here. However, the concentration of acid in the shear thinning gel is limited by regulations and the quantity of viscosity modifiers. It would be desirable to have a way to retain acid cleaners against leakage without the drawbacks of shear-thinning gels.

Accordingly, an embodiment provides a system and method for cleaning a surface or a quartz sleeve, surface, or UV-transparent material. In an embodiment, an acidic cleaning composition may be encapsulated in a polymer coating to make a cleaning compound. In an embodiment the cleaning composition may be contained in a polymer material. In an embodiment, polymer coating may dissolve at a pH above a target value above the polymer material pH dissolution point. The polymer coating may dissolve above a target pH to release the cleaning composition. The composition of the polymer material may determine the dissolution pH. In other words, once a target pH is reached the cleaning composition may be released to lower the pH. The target pH may be an acidic pH which releases an acidic cleaning composition further lowering the pH. In an embodiment, the compound may be placed in a canister. The canister may have a volume adjacent to the sleeve but separate from an outer volume. The outer volume may comprise a fluid for treatment or disinfection in a facility. In an embodiment, the polymer coating comprises soluble material. In an embodiment, the polymer coating may comprise acrylates such as methacrylic acid, ethyl acrylate, methylmethacrylate, butylmethacrylate, or a combination thereof. In an embodiment, the cleaning composition may contain phosphoric acid, citric acid, sulfonic acid, sodium bisulfate, or combination thereof. The cleaning composition may further comprise a base such as alkylamines, dialklylamines, trialkylamines, quats (quaternary ammonium), polymers with amino or (alkyl or aryl) amino substituents groups, polymers with nitrogen-containing hetero cyclic groups, acrylamide, polymers an copolymers of acrylamide, vinyl pyrollidone, polyvinyl pyrollidone, copolymers of vinyl pyrollidone, methacrylamide, poly methacrylamide, copolymers of acrylamide, ammonia, or the like or combination thereof. The cleaning composition may clean the quartz sleeve, surface, or UV-transparent material. In an embodiment, the compound may also contain other ingredients such as gelatin, a pelletizing agent, an anti-caking agent, or the like.

The illustrated example embodiments will be best understood by reference to the figures. The following description is intended only by way of example, and simply illustrates certain example embodiments.

Figure 1:
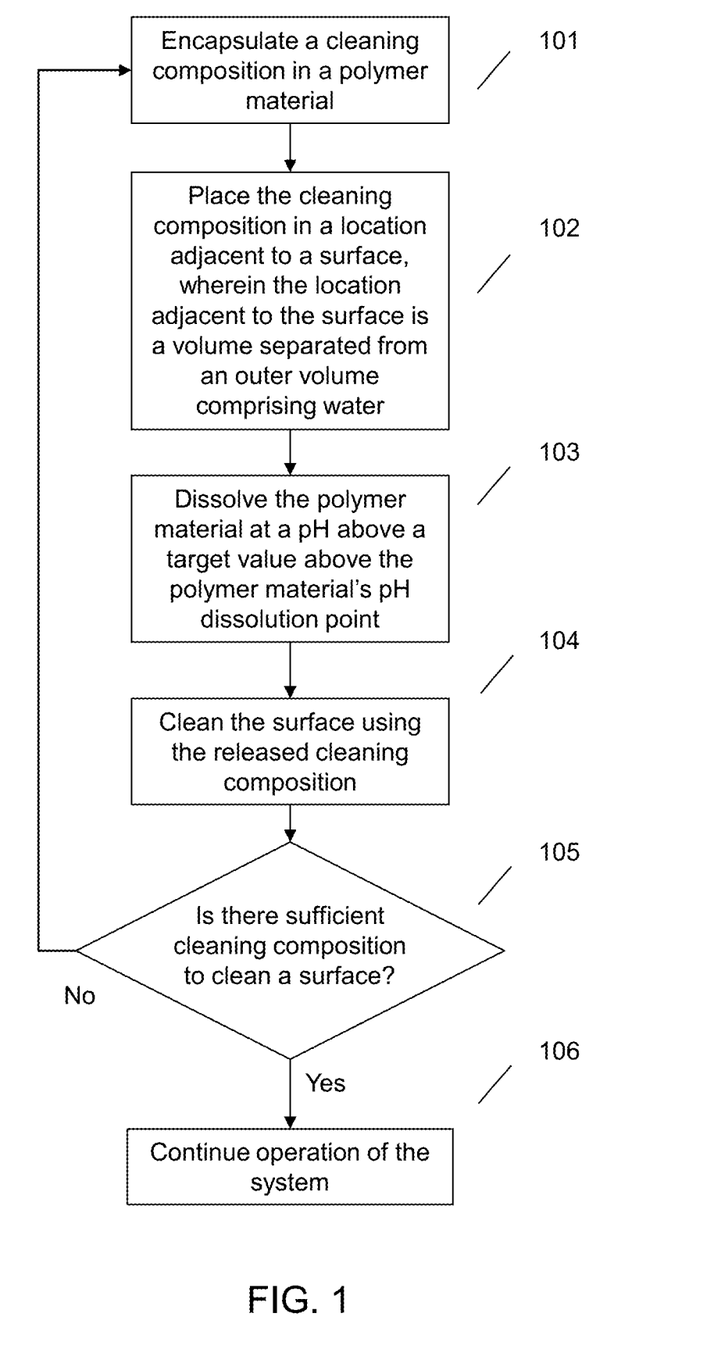
FIG. 1 illustrates a flow diagram of an example pH dependent soluble polymers in an embodiment.

Referring to FIG. 1, an example system and method for cleaning a quartz sleeve, surface, or UV-transparent material is illustrated. As an example, a quartz sleeve may be the surface to be cleaned, however, other surfaces are disclosed and contemplated. In an embodiment, the quartz sleeve may be a sleeve around a UV lamp. In an embodiment, the quartz sleeve may have a canister around the sleeve. The canister may form a fluidically separated seal from the inside of the canister adjacent to the sleeve and the outer volume outside the canister. The canister may be capable of moving or sliding along the longitudinal axis of the sleeve. The canister may serve a cleaning function. For example, a canister may comprise one or more wipers to clean the sleeve. In an embodiment, the wiper may comprise an actuator and/or a connecting rod. In an embodiment, the canister may comprise of a compartment that houses a cleaner or a cleaning composition that is separated and shielded from the UV light source. The cleaner or cleaning agent may be a cleaning composition. The cleaning composition may be encapsulated in a polymer coating. The polymer coating may dissolve above a target pH. In other words, as an acid becomes exhausted for cleaning, a rise in pH may dissolve a polymer coating, release an acid, and clean the sleeve in the area of the canister upon the sleeve.

At 101, in an embodiment, an acid composition may be encapsulated or embedded in a polymer coating. In an embodiment, acid composition may be referred to as a cleaning composition or compound. In an embodiment, the polymer encapsulated acid composition may be referred to as a cleaning compound. In other words, the cleaning compound may contain different ingredients as described and disclosed herein. In an embodiment, the cleaning compound, which may be made in the form of one or more pills, may comprise different cleaning materials. In an embodiment, the acid composition may include phosphoric acid, citric acid, sulfonic acid, sodium bisulfate, or the like. The acid composition may be homogeneous such as comprising a single type of acid. Alternatively, the acid composition may be heterogeneous and comprise two or more of the listed acid types. The acid composition may be in a powder, liquid, gel, or the like form.

In an embodiment, the polymer coating may be a soluble polymer that dissolves at a target pH or in a pH range. The polymer may be an acidic/hydrophilic monomer, a hydrophobic monomer, or the like. Acidic monomers may be used to lower a pH after dissolution of the polymer coating. The coating may be an enteric coating. In an embodiment, the polymer may comprise methacrylic acid (MAA), ethyl acrylate (EA), methylmethacrylate (MMA), butylmethacrylate (BMA), or the like. As an example, a polymer may comprise 50% MAA and 50% EA, 80% MAA and 20% EA, 90% MAA and 10% EA, or the like. As another example, the polymer may comprise 90% MAA and 10% MMA. As a further example, the polymer may comprise 90% MAA and 10% BMA. Other ratios or percentages are disclosed and contemplated. Example ratios are for illustrative purposes.

In an embodiment, the compound may contain other ingredients. For example, the compound may comprise a colorant, a UV blocker, a pH sensitive indicator, gelatin, a pelletizing agent, an anti-caking agent, a plasticizer, a stabilizer, an emulsifier, a glidant, a binder, a lubricant, a pigment, a solvent, or the like. The other ingredients may maintain a part of the compound in a certain state, such as a solid, liquid, or powder. In an embodiment, the other ingredients may be necessary for the stability of the compound in storage or until a time when the polymer coating or material dissolves in pH range to release the cleaning composition.

At 102, in an embodiment, the method and system may place a quantity of the cleaning compound in a location adjacent to a quartz sleeve. In an embodiment, the location adjacent to the quartz sleeve may be a fluidically separated volume from an outer volume. For example, a UV lamp may be in a quartz sleeve and in a chamber of fluid to be disinfected. A canister may be placed upon the quartz sleeve and maintain a location adjacent to the sleeve with a volume. The volume within the canister may be fluidically separated from an outer volume which may be a fluid for disinfection.

Figure 4:
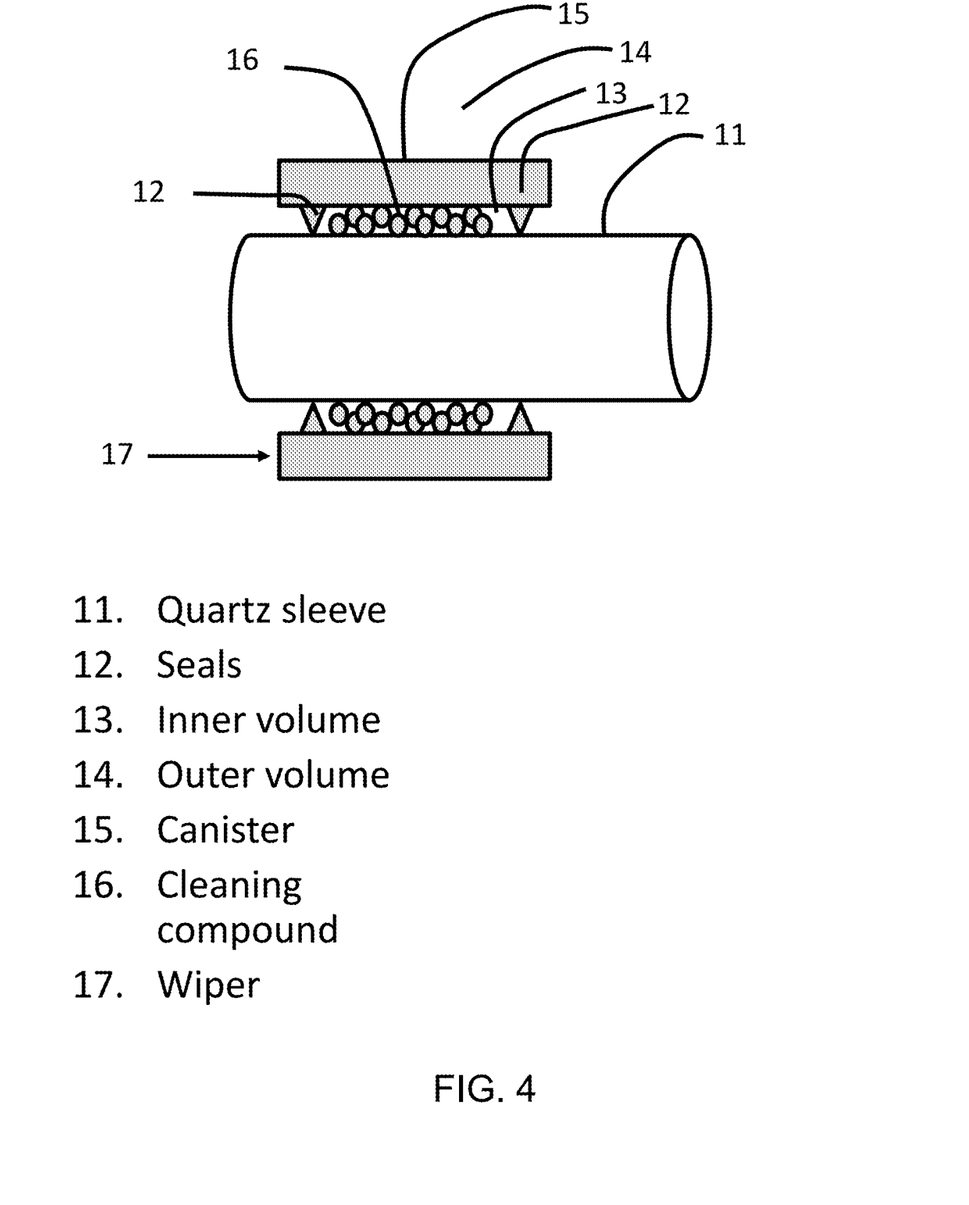
FIG. 4 illustrates an example of a cleaning system incorporating a pH-dependent soluble composition.

Referring to FIG. 4, in an embodiment, the canister 15 may be a cylindrical shape around a cylindrical sleeve 11 in which the diameter of the canister is greater than the diameter of the sleeve. Other cross sectional shapes are disclosed and contemplated. A cylinder is illustrative. In an embodiment, the canister may move along the longitudinal length of the sleeve. The canister may retain the cleaning compound 16 in the form of one or more blocks, pills, or other shapes. One or more canisters may be combined in a cleaning system or a wiper 17. In an embodiment, the wiper may be referred to as a wiper assembly. In an embodiment, these canisters and associated wiper may be moved along the quartz sleeve. In an embodiment, the wiper may comprise an actuator and connecting rod. In other words, the actuator and connecting rod may move the wiper or cleaning system. The actuator could be a hydraulic cylinder, an electric actuator, a pneumatic actuator or other type of actuator. There may be one or more canisters for each sleeve. The canister may have seals 12 that separate a volume inside the canister 13 against or upon the surface of the sleeve, separating that volume from an outer volume 14. For example, a gasket, seal, O-ring, or the like may fill the gap of the outside diameter of the sleeve and in the inside diameter of the canister. In an embodiment, a cleaning function may remove fouling, or the like, form the sleeve. The canister may also incorporate a scraper to physically remove fouling materials from the surface when the wiper is moved along the surface.

In an embodiment, the cleaning compound may be not adjacent to the cleaning surface but is instead located in a remote reservoir. The remote reservoir could be located above the water level in an open-channel (free surface) treatment system, or could be surrounded by water. Water may be introduced into the remote reservoir, and if that water has a pH above the dissolution point of the polymer the polymer will dissolve and release an acidic cleaning substance. This cleaning substance may cause the pH of the water in the remote reservoir to drop. This low-pH water may then be circulated, using a pump, gravity, or other means, to the surface that is to be cleaned. This could entail circulating the low-pH solution into cleaning canisters located adjacent the quartz sleeve. Those canisters may be moved along the sleeve, using actuators and/or a connecting rod, in order to clean the length of the sleeve.

In an embodiment, the cleaning compound in the form of one or more pills may be introduced to the inside of a canister. In an embodiment, the pills are in the volume adjacent to the sleeve and fluidically separated from an outside volume such as fluid for treatment. In an embodiment, the pills may be added manually or automatically. For example, when the pills become depleted or dissolved, a user may manually add more pills to the canister. For example, a user or system may detect a depletion of pills or an increase in pH within a canister and manually add more pills to the canister. In an embodiment, a sensor may detect a pH level out of a desired range and add more pills to a canister. As an example, the canister, which may move along the length of the sleeve, may move to a position out of a fluid where a hopper may dispense more pills. Detection of a low level of pills may be detected using visual inspection of the one or more pills condition, the cleaning performance of a sleeve, a pH sensor, a color or visual indicator, or the like.

At 103, in an embodiment, the system and method dissolve the polymer coating or material above a target pH. In an embodiment, the dissolving may release the acid or cleaning composition. In an embodiment, a use of the cleaning compound in a canister is to clean a sleeve. For example, the polymer coating encapsulates an acid composition. If an environment or the volume of the canister fluid becomes too alkaline, then the polymer coating may dissolve and release the cleaning composition. The cleaning composition may clean the sleeve. In other words, the system and method may utilize the cleaning compound or pills as a way to create a set point or range of an acceptable pH for the cleaning of the sleeve by maintaining a pH in a canister. A lower level of acid in a canister may lead to the dissolving of a polymer material to release more acid. A proper acidic environment may preserve further compound from dissolving so it may be dissolved at a later time.

Figure 2:
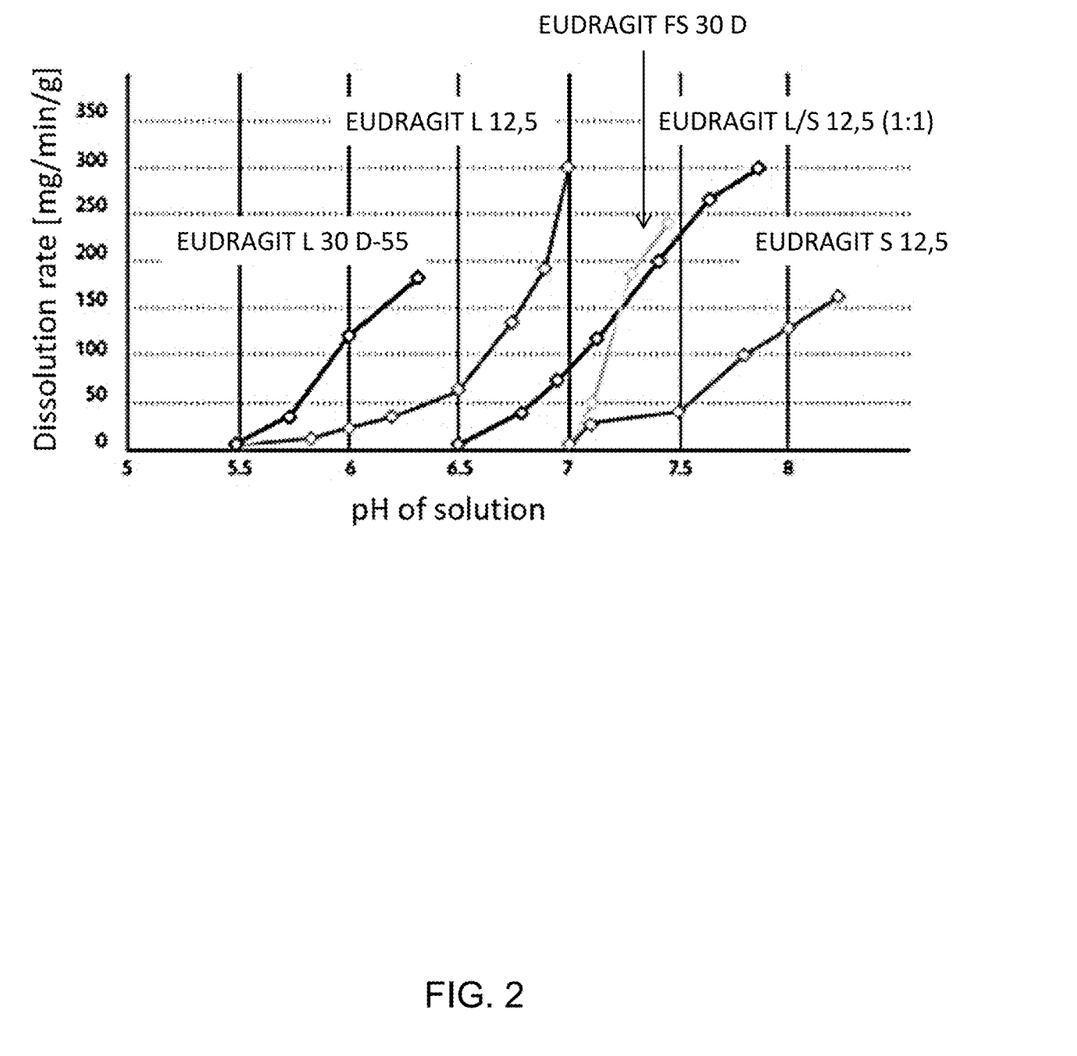
FIG. 2 illustrates example data of dissolution rates based on a pH of a solution for different enteric coatings comprising polymers.

Referring to FIG. 2, in an embodiment, example dissolution rates of polymers and mixtures are illustrated. Inorganic fouling on the quartz sleeves in UV systems degrades performance because it blocks the UV light from reaching the fluid. Acid solutions may be effective sleeve cleaners without damaging the quartz substrate. Conventionally, ActiClean Gel, a clay-based acid solution available from Trojan Technologies, London, Ontario Canada (ActiClean is a registered trademark of Trojan Technologies in the United States and other countries), may be used in a physical wiper system to clean fouling materials from the sleeves. Liquid cleaning solutions are subject to dilution from leakage resulting from wiper seal wear.

In an embodiment, an acidic cleaning solution could be a substance that retained the acid until the pH of the solution rose when the acid was depleted. Enteric coatings may be commercially available pharmaceutical polymers designed to protect and release active ingredients at different positions of the gastrointestinal tract. For example, one type of enteric coating has a pH-dependent solubility. In other words, it does not dissolve in stomach acid, but dissolves in the higher pH conditions of the intestine. If this characteristic could be tailored, it may act as an acid dispenser, dispensing acid only when the pH of the solution went above a threshold.

In an embodiment, methacrylic acid-based enteric coatings, which may possess the proper dissolution response to pH (elevated at higher pH and negligible at lower pH) and be modifiable based on monomers type and monomer ratios. These coatings are primarily under the Kollicoat MAE brand (produced by BASF, Ludwigshafen, Germany, registered trademarks of BASF in the United States and other countries) and Evonik under the Eudragit brand (produced by Evonik, Essen, Germany, registered trademarks of Evonik in the United States and other countries). Enteric coated materials may have a number of potential advantages over liquid acid solutions. For example, they are a solid, and retained even if wiper seals leak. They are pH sensitive so they will recharge the canister with fresh acid upon wiper seal leaks and acid "consumption". They are GRAS (generally regarded as safe), and are approved for human consumption. Enteric coatings may also completely dissolve when depleted, so there would be a visual indication that replacement may be required.

Figure 3:
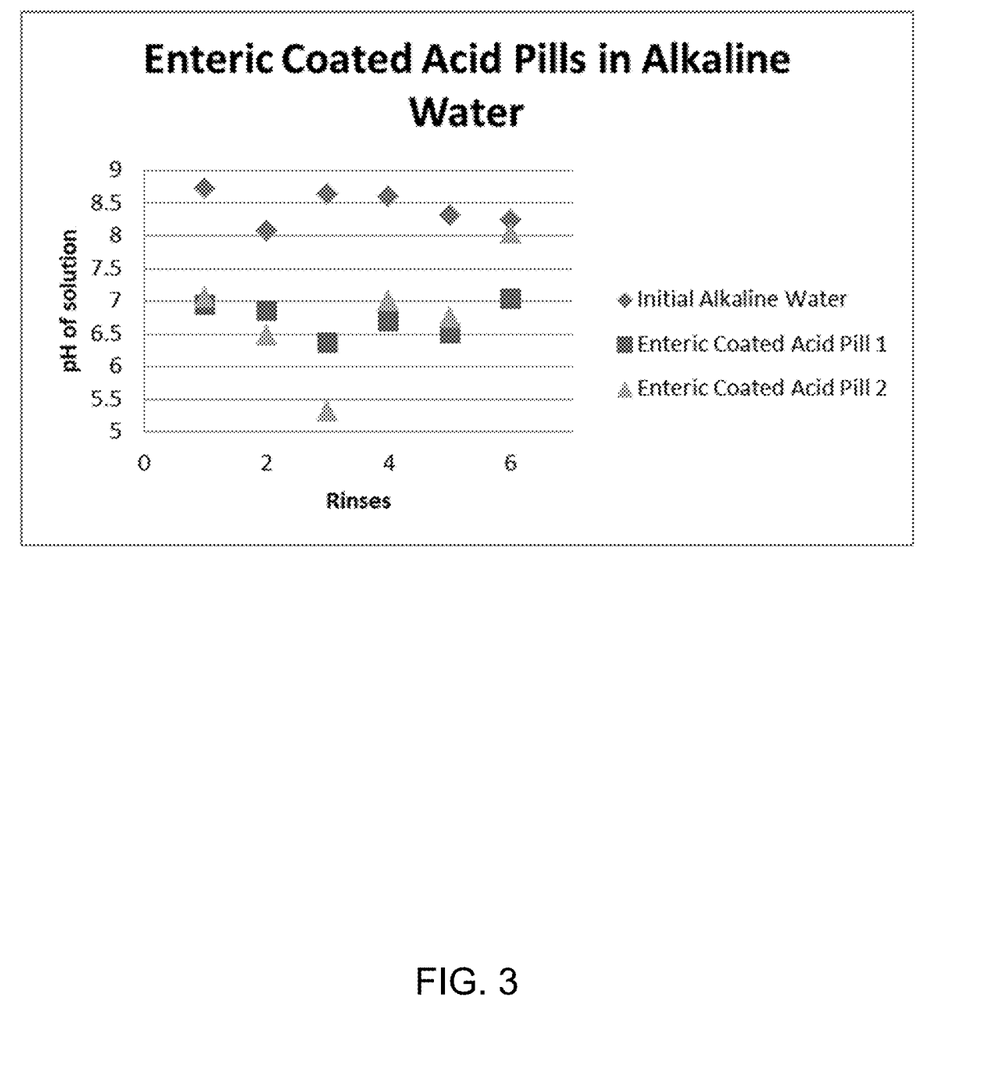
FIG. 3 illustrates example data of a pH of a solution based on the number of rinses for release of an acid using different coatings.

Referring to FIG. 3, in an embodiment, example enteric coatings in an alkaline water solution are illustrated. For example, the accelerated aging of the enteric coated pills may be repeated with alkaline water, to demonstrate the pH dissolution point of the enteric coating in the solution. The alkaline water solution was more basic than the pH dissolution point of the enteric coating, resulting in the pH of the water decreasing to the pH dissolution point of the enteric coating and stopping. When the coating ruptures, the acid in the pill releases to the water lowering the pH further and stopping all other dissolution of the enteric coating, as seen during the $3^{rd}$ rinse. The enteric coating is completely consumed by the $7^{th}$ rinse for enteric coated acid pellet #2, resulting in the pH of the water barely changing from the initial alkaline pH.

At 104, in an embodiment, the system and method may clean the quartz sleeve. In an embodiment, the cleaning may be performed by the acid composition. The acid composition may be released by dissolving the polymer coating at a target pH. As the pH within a canister becomes more alkaline, the pH sensitive soluble polymer coating may dissolve to release an acid composition. In an embodiment, a pH less than or around 3.0 may remove fouling from a quartz sleeve without damage to the sleeve. In an embodiment, the pH may be in a preferred range of 2.5-4.0. A pH higher than the desired set point may release acid. In an embodiment, the polymer coating may be designed to dissolve above a given pH.

At 105, in an embodiment, the system and method may determine if there is a proper cleaning of the sleeve. For example, a visual inspection may indicate pill replenishment may be necessary. As another example, an automated system may use sensors to determine a pH of a canister is outside acceptable levels and add pills to the canister. As a further example, sensors, such as optical sensors, may determine if a sleeve is properly cleaned or fouling is within acceptable levels. Additionally or alternatively, the system may output an alarm, log an event, provide visual indication, or the like. If the system and method is functioning nominally, the system and method may continue to operate at 106. The output may be provided to a device in the form of a display, printing, storage, audio, haptic feedback, or the like. Alternatively or additionally, the output may be sent to another device through wired, wireless, fiber optic, Bluetooth®, near field communication, or the like.

An embodiment may use an alarm to warn of a measurement, pH, fouling, or the like being outside acceptable levels. An embodiment may use a system to shut down water output or shunt water from sources with unacceptable UV treatment. For example, the device may use a relay coupled to an electrically actuated valve, or the like. The system may connect to a communication network. The system may alert a user or a network. This alert may occur whether a sleeve is properly cleaned or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if a pH or fouling reaches a threshold or set point. Alarms or logs may be analyzed in real-time, stored for later use, or any combination thereof. For example, an alarm may indicate a current concentration of a component is above a desired threshold. If pill replenishment is required, the method or system may return to a previous step such as 101 or 102.

The various embodiments described herein thus represent a technical improvement to conventional methods for cleaning a UV lamp sleeve. Using the techniques as described herein, an embodiment may use a system and method to maintain a pH in a canister for cleaning of a sleeve.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions or acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for cleaning a sleeve of an ultraviolet light source, comprising:
    providing the ultraviolet light source for disinfection of a fluid, wherein the sleeve surrounds the ultraviolet light source;
    encapsulating a cleaning composition in a polymer material to form a compound;
    placing the compound in a location adjacent to the sleeve, wherein a canister around and in contact with the sleeve encapsulates the compound against the sleeve;
    dissolving the polymer material at a pH above a polymer material pH dissolution point, wherein the dissolving releases the cleaning composition; and
    cleaning the sleeve using the released cleaning composition.

2. The method of claim 1, wherein the cleaning composition is selected from the group consisting of: phosphoric acid, citric acid, sulfonic acid, and sodium bisulfate.

3. The method of claim 1, wherein the cleaning composition further comprises a base selected from the group consisting of: alkylamines, dialklylamines, trialkylamines, quaternary ammonium compounds, polymers with amino groups, polymers with nitrogen-containing hetero cyclic groups, arcylamide, polymers of acrylamide, vinyl pyrollidone, polyvinyl pyrollidone, copolymers of vinyl pyrollidone, metharcylamide, polymetharcylamide, copolymers of acrylamide, and ammonia.

4. The method of claim 1, wherein the polymer material pH dissolution point is based upon a composition of the polymer material.

5. The method of claim 1 wherein the polymer material comprises an acidic monomer.

6. The method of claim 1, wherein the polymer material comprises an acrylate based component.

7. The method of claim 1, wherein the cleaning further comprises a wiper, wherein an actuator moves the wiper and the cleaning composition across the sleeve.

8. The method of claim 1, the compound further comprises an ingredient selected from the group consisting of: gelatin, a pelletizing agent, an anti-caking agent, a plasticizer, a stabilizer, an emulsifier, a glidant, a binder, a lubricant, a pigment, a filler, a crosslinking agent, and a solvent.

* * * * *